(12) United States Patent
Iacoangeli et al.

(10) Patent No.: US 12,221,438 B2
(45) Date of Patent: Feb. 11, 2025

(54) CONTINUOUS PROCESS FOR THE PREPARATION OF TRAZODONE

(71) Applicant: AZIENDE CHIMICHE RIUNITE ANGELINI FRANCESCO A.C.R.A.F. S.p.A., Rome (IT)

(72) Inventors: Tommaso Iacoangeli, Rome (IT); Leonardo Mario Moro, Aprilia (IT); Giuliano Caracciolo Torchiarolo, Aprilia (IT); Claudia Cavarischia, Rome (IT); Guido Furlotti, Rome (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 1212 days.

(21) Appl. No.: 16/967,337

(22) PCT Filed: Feb. 5, 2019

(86) PCT No.: PCT/EP2019/052690
§ 371 (c)(1),
(2) Date: Aug. 4, 2020

(87) PCT Pub. No.: WO2019/154770
PCT Pub. Date: Aug. 15, 2019

(65) Prior Publication Data
US 2021/0032243 A1     Feb. 4, 2021

(30) Foreign Application Priority Data
Feb. 7, 2018   (EP) ..................... 18155470

(51) Int. Cl.
C07D 471/04   (2006.01)
B01J 14/00    (2006.01)
B01J 19/00    (2006.01)
B01J 19/18    (2006.01)

(52) U.S. Cl.
CPC ............ *C07D 471/04* (2013.01); *B01J 14/00* (2013.01); *B01J 19/0093* (2013.01); *B01J 19/18* (2013.01); *B01J 2219/00029* (2013.01); *B01J 2219/00033* (2013.01)

(58) Field of Classification Search
CPC ....................................................... B01J 19/18
See application file for complete search history.

(56) References Cited

U.S. PATENT DOCUMENTS

| 3,381,009 A | 4/1968 | Palazzo et al. |
| 4,254,124 A | 3/1981 | Morrow |
| 5,900,485 A | 5/1999 | Lei et al. |

FOREIGN PATENT DOCUMENTS

| CN | 101772490 A | 7/2010 |
| CN | 105777745 A | 7/2016 |
| EP | 0027002 A1 * | 4/1981 |
| EP | 1 108 722 B1 | 4/2005 |
| EP | 2 178 850 B1 | 9/2014 |
| HU | 201324 B | 10/1990 |
| WO | WO 92/06083 A1 | 4/1992 |
| WO | WO-2017166050 A1 * | 10/2017 |

OTHER PUBLICATIONS

Gutmann et. al (Angew. Chem. Int. Ed. 2015, 54, 6688-6728.) (Year: 2015).*
Combined Chinese Office Action and Search Report issued Oct. 21, 2022 in Chinese Patent Application No. 201980011910.0 (with English translation), 10 pages.
Sulcova, A., "Multimodal Pharmacological Actions of Trazodone," Psychiatrie, 2015, vol. 19, No. 1, pp. 49-52.
Bryant, S. G. et al., "A Drug Utilization Review of Prescribing Patterns for Trazodone Versus Amitriptyline," Journal of Clinical Psychiatry, 1990, vol. 51, pp. 27-29. (3 total pages).
Beasley, C. M. et al., "Fluoxetine Versus Trazodone: Efficacy and Activating-Sedating Effects," Journal of Clinical Psychiatry, 1991, vol. 52, pp. 249-299.
Kasper, S. et al., "A comparative, randomised, double-blind study of trazodone prolonged-release and paroxetine in the treatment of patients with major depressive disorder," Current Medical Research and Opinion, 2005, vol. 21, No. 8, pp. 1139-1146.
Munizza, C. et al., "A comparative, randomized, double-blind study of trazodone prolonged-release and sertraline in the treatment of major depressive disorder," Current Medical Research and Opinion, 2006, vol. 22, No. 6, pp. 1703-1713.
Cunningham, L. A. et al., "A Comparison of Venlafaxine, Trazodone, and Placebo in Major Depression," Journal of Psychopharmacology, 1994, vol. 14, No. 2, pp. 99-106.
Fagiolini, A. et al., "Rediscovering Trazodone for the treatment of Major Depressive Disorder," CNS Drugs, 2012, vol. 26, pp. 1033-1049.
March, J. "Reactions, Mechanisms and Structure," Advanced Organic Chemistry, IV ed., 1992, p. 370.
pp. 228 and 458 of McGraw-Hill Dictionary of Engineering, 2E, Copyright © 2003 by The McGraw-Hill Companies, Inc.

(Continued)

*Primary Examiner* — John S Kenyon
*Assistant Examiner* — Rehana Ismail
(74) *Attorney, Agent, or Firm* — Oblon, McClelland, Maier & Neustadt, L.L.P.

(57) ABSTRACT

The present invention relates to an improved process for the preparation of trazodone. In particular, the present invention relates to a continuous process for the preparation of trazodone. More in particular, the present invention relates to a new method for the preparation of trazodone, said method comprising at least one step consisting of a continuous process performed in a flow reactor.

21 Claims, 4 Drawing Sheets

(56) References Cited

OTHER PUBLICATIONS

Anderson, N.G. "Practical Use of Continuous Processing in Developing and Scaling Up Laboratory Processes," Organic Process Research & Development, Nov. 1, 2001, vol. 5, No. 6, XP055468733, pp. 613-621.
International Search Report issued on Mar. 14, 2019 in PCT/EP2019/052690 filed on Feb. 5, 2019.

* cited by examiner

CONTINUOUS PROCESS FOR THE PREPARATION OF TRAZODONE

CROSS REFERENCE TO RELATED APPLICATIONS

This application is a 371 of International Patent Application No. PCT/EP2019/052690, filed Feb. 5, 2019, and claims priority to European Patent Application No. 18155470.0, filed Feb. 7, 2018, both of which are incorporated herein by reference in their entireties.

FIELD OF THE INVENTION

The present invention relates to an improved process for the preparation of trazodone carried out in a continuous mode in a flow reactor.

STATE OF THE ART

Trazodone, or 2-[3-[4-(3-chlorophenyl)-1-piperazinylpropyl]-1,2,4-triazolo[4,3-a]pyridin-3(2H)-one, is a multifunctional and multimodal antidepressant drug acting through 5-HT receptors and inhibiting the 5-HT transporter.

Trazodone is classified as a 'multimodal' antidepressant (Sulcova A., Psychiatrie, 2015, 19 (1), 49-52), with a resulting pharmacological profile distinct from that of Selective Serotonin Reuptake Inhibitors (SSRIs) and Serotonin and Norepinephrine Reuptake Inhibitors (SNRIs).

Since its introduction in the 1970's, trazodone has proved its antidepressant equivalence to other well-known antidepressants belonging to different classes, such as tricyclics (Bryant S. G. et al., Journal of Clinical Psychiatry, 1990, 51, 27-29), SSRIs including fluoxetine (Beasley C. M. et al., Journal of Clinical Psychiatry, 1991, 52, 294-299), paroxetine (Kasper S. et al., Current Medical Research and Opinion, 2005, 21 (8), 1139-1146), sertraline (Munizza C. et al., Current Medical Research and Opinion, 2006, 22 (6), 1703-1713) and SNRIs such as venlafaxine (Cunningham L. A. et al., Journal of Clinical Psychopharmacology, 1994, 14 (2), 99-106).

Overall, trazodone is considered effective and well tolerated, with the most common adverse events (AEs) being somnolence/sedation, headache, dizziness and dry mouth (Fagiolini A. et al., 2012, 26, 1033-1049).

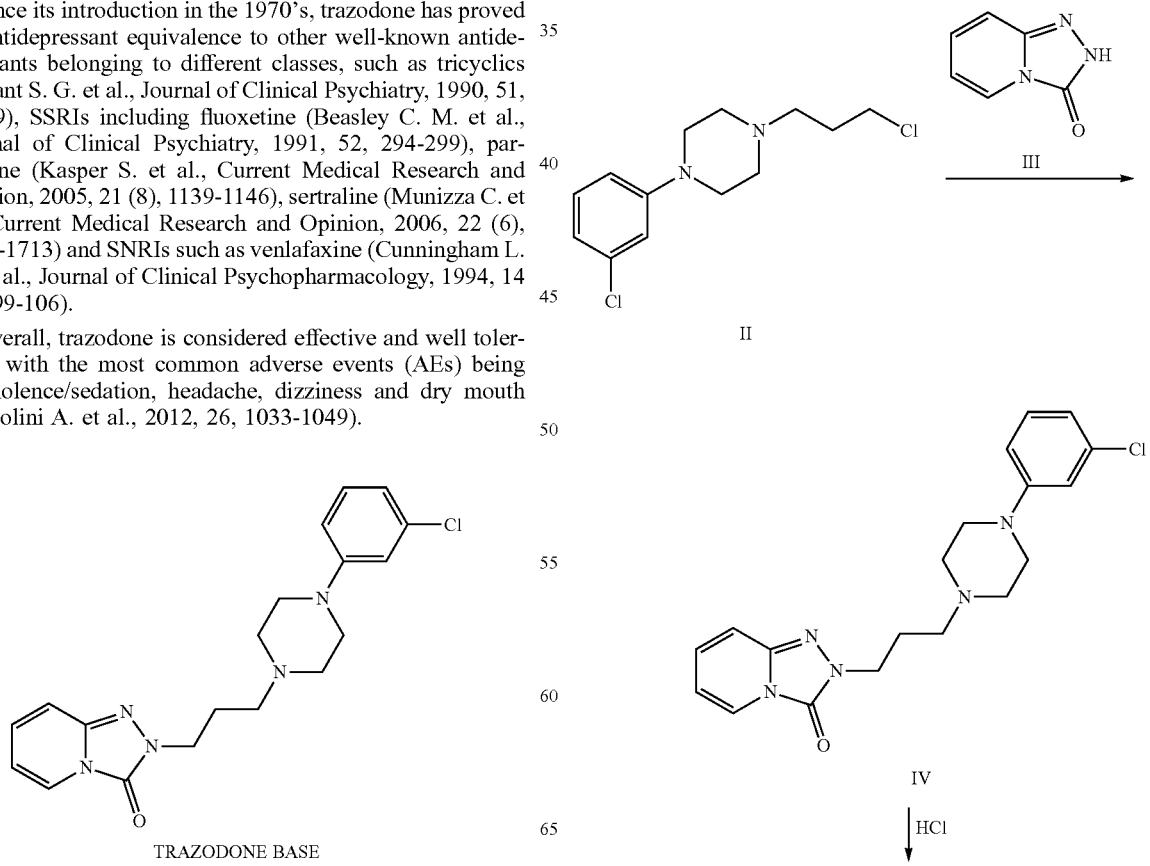

TRAZODONE BASE

TRAZODONE HYDROCHLORIDE

Trazodone is currently produced in the free base form and as a pharmaceutically acceptable salt of acid addition, both depicted above. The preferred form is the hydrochloride salt obtained by treatment of the free base with hydrochloric acid.

Several methods for the synthesis of trazodone are known in the art.

U.S. Pat. No. 3,381,009, by the present Applicant, discloses different synthetic routes for the synthesis of trazodone base (IV), among which the reaction between N-(3-chlorophenyl)-N'-(3-chloropropyl)-piperazine (II) and s-triazolo-[4,3-a]-pyridin-3-one (III), as depicted in the first step of the scheme below.

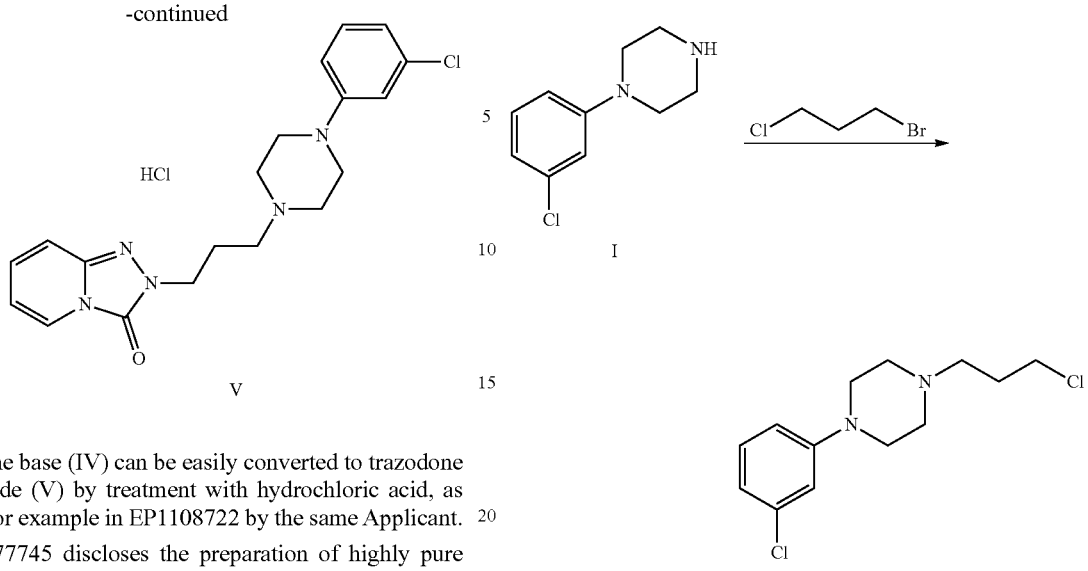

Trazodone base (IV) can be easily converted to trazodone hydrochloride (V) by treatment with hydrochloric acid, as described for example in EP1108722 by the same Applicant.

CN105777745 discloses the preparation of highly pure trazodone and trazodone hydrochloride from N-(3-chlorophenyl)-N'-(3-chloropropyl)-piperazine and pyridine triazolone, in organic solvents and by the addition of a base. The reaction is said to be carried out at the reflux temperature.

The patent HU201324B describes the above depicted synthesis of trazodone from N-(3-chlorophenyl)-N'-(3-chloropropyl)-piperazine (II) and s-triazolo-[4,3-a]-pyridin-3-one (III), carried out in a dipolar aprotic solvent such as dimethylacetamide or dimethylformamide by adding an alkali metal carbonate in alternative to sodium hydroxide and an alkali metal iodide in a catalytic quantity. This synthesis is said to be carried out in a few hours and to provide good quality trazodone base in high yields.

On its part, N-(3-chlorophenyl)-N'-(3-chloropropyl)-piperazine (II) can be easily synthesized reacting m-chlorophenyl-piperazine (I) with 1-bromo-3-chloropropane (see scheme below), as described for example in EP0027002 or U.S. Pat. No. 5,900,485.

Synthetic methods described in the art generally involve long reaction time (hours) and high amounts of toxic reagents to be handled.

SUMMARY OF THE INVENTION

The present invention relates to the synthesis of trazodone in a continuous mode by reaction of N-(3-chlorophenyl)-N'-(3-chloropropyl)-piperazine (II) and s-triazolo-[4,3-a]-pyridin-3-one (III), to obtain trazodone base (IV).

Trazodone base (IV) is then converted without any further purification into trazodone hydrochloride (V) (Scheme 1 below), obtained with a very low content of alkylating substances, said low level being not higher than 15 ppm, preferably 10 ppm, even more preferably 5 ppm, and more preferably below 2.5 ppm, and at least comparable to that achieved by the purification process described in EP2178850 by the same Applicant.

Scheme 1

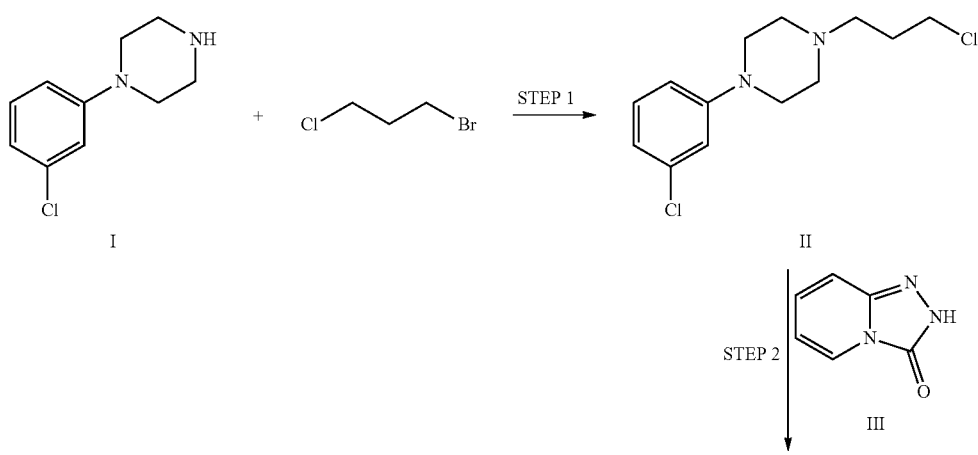

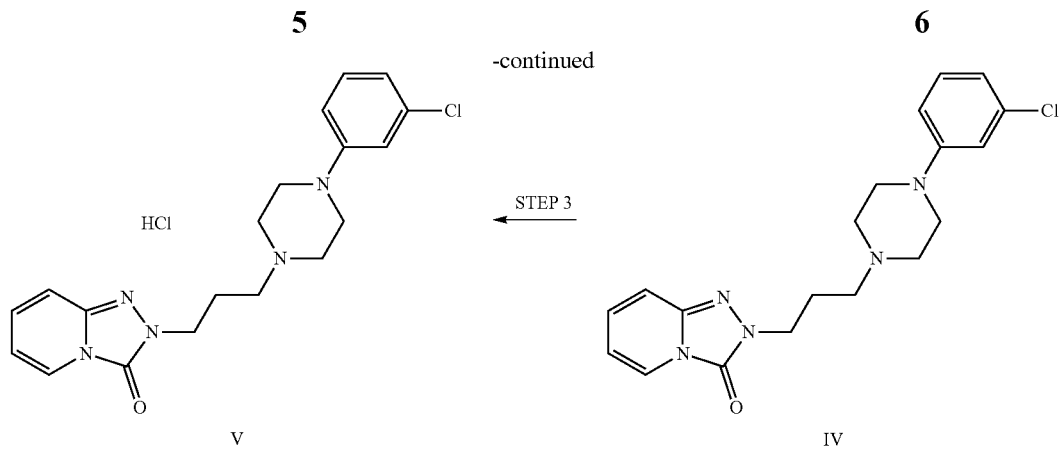

The alkylating substances involved in the above described reactions are, for example, 1-bromo-3-chloropropane, used for obtaining compound (II), and compound (II) itself.

Common reaction techniques used in the so called "batch" processes force the operator to come into contact with high amounts of said substances.

In addition, long reaction time at high temperatures gives as a drawback a breakdown of reagents, which has an adverse effect on both yield and quality of the final product.

The Applicant has felt that there is a need for a safer and more efficient process for the preparation of trazodone.

Such a need is met by the present invention with a continuous process carried out in a flow reactor allowing to produce trazodone base (IV), which is further converted into trazodone hydrochloride (V), more efficiently, with extremely reduced reaction times and similar or higher yields and quality than those currently obtained with the known "batch" procedures, thus resulting in a more efficient, cost effective and environmental friendly process.

Thus, the Applicant has developed a new method for the preparation of trazodone, according to Scheme 1 above, said method comprising at least one step consisting of a continuous process performed in a flow reactor.

In particular, the Applicant has developed a continuous process for the preparation of trazodone, said continuous process comprising a step for the preparation of trazodone base (IV) in a flow reactor starting from the key intermediate N-(3-chlorophenyl)-N'-(3-chloropropyl)-piperazine (II) and s-triazolo-[4,3-a]-pyridin-3-one (III) (step 2, Scheme 1 above).

Then, the thus obtained trazodone base (IV) is converted into the corresponding hydrochloride (V) with methods known in the art (step 3, Scheme 1 above).

Finally, the Applicant has also developed a continuous process for the preparation of trazodone starting from m-chlorophenyl-piperazine (I) and 1-bromo-3-chloropropane, which comprises the continuous process described above (step 1 and 2, Scheme 1 above).

According to a preferred embodiment, N-(3-chlorophenyl)-N'-(3-chloropropyl)-piperazine (II), key intermediate in the synthesis of trazodone, is obtained with high yields and purity, and with only a few minutes of reaction time, performing also this reaction via a continuous process, in an alkaline aqueous media and at temperatures higher than 70° C., in a flow reactor.

The key intermediate (II) is converted to trazodone base (IV), with high yields and purity, and with only few minutes of reaction time, performing the reaction via a continuous process, in alkaline aqueous media and at temperatures higher than 90° C., in a flow reactor as described above.

This result is even more surprising due to the fact that it is well recognized in the art that alkyl halides, such as N-(3-chlorophenyl)-N'-(3-chloropropyl)-piperazine (II), are instable in alkaline aqueous solutions at elevated temperatures, as disclosed for example in U.S. Pat. No. 4,254,124, HU 201324, and in J. March, Advanced Organic Chemistry, IV ed., 1992, pag. 370.

The present invention thus allows to obtain N-(3-chlorophenyl)-N'-(3-chloropropyl)-piperazine (II) and trazodone base (IV) in high yield and purity, with short reaction times, drastically reducing amount need and handling of reagents, with a dramatic improvement in the safety and efficiency of the production process when compared to classical "batch" methodologies.

The trazodone base (IV) thus obtained is directly converted, by simple treatment with concentrated hydrochloric acid, into trazodone hydrochloride (V) with a quality comparable to that disclosed in EP2178850B1, without further purification.

Therefore, according to a main aspect, the present invention provides a continuous process for the preparation of trazodone base (IV) and trazodone hydrochloride (V) starting from N-(3-chlorophenyl)-N'-(3-chloropropyl)-piperazine (II) and s-triazolo-[4,3-a]-pyridin-3-one (III), according to Step 2 of the Scheme 1 above, comprising continuously mixing in a flow reactor an alkaline aqueous solution of s-triazolo-[4,3-a]-pyridin-3-one (III) and an organic solution of N-(3-chlorophenyl)-N'-(3-chloropropyl)-piperazine (II), and continuously recovering trazodone base (IV), preferably with a conversion yield of at least 70%, more preferably at least 80%, even more preferably 90%. Even more preferably conversion yields are equal to or above 95%, 97%, 98% or are quantitative.

The invention further provides a continuous process for the preparation of trazodone base (IV) starting from m-chlorophenyl-piperazine (I) and 1-bromo-3-chloropropane, wherein the process of Step 2 above is preceded by the preparation of N-(3-chlorophenyl)-N'-(3-chloropropyl)-piperazine (II), according to Step 1 of Scheme 1 above, carried out in a continuous mode in a flow reactor.

According to a further aspect, the invention relates to the preparation of N-(3-chlorophenyl)-N'-(3-chloropropyl)-piperazine (II) starting from m-chlorophenyl-piperazine (I) and 1-bromo-3-chloropropane, according to Step 1 of Scheme 1 above, in a continuous mode in a flow reactor.

BRIEF DESCRIPTION OF THE DRAWINGS

The present invention will be better understood by reading the following examples, given by way of illustration and not of limitation, to be read with the accompanying drawings, wherein.

DETAILED DESCRIPTION OF THE INVENTION

Definitions

Figure 1:
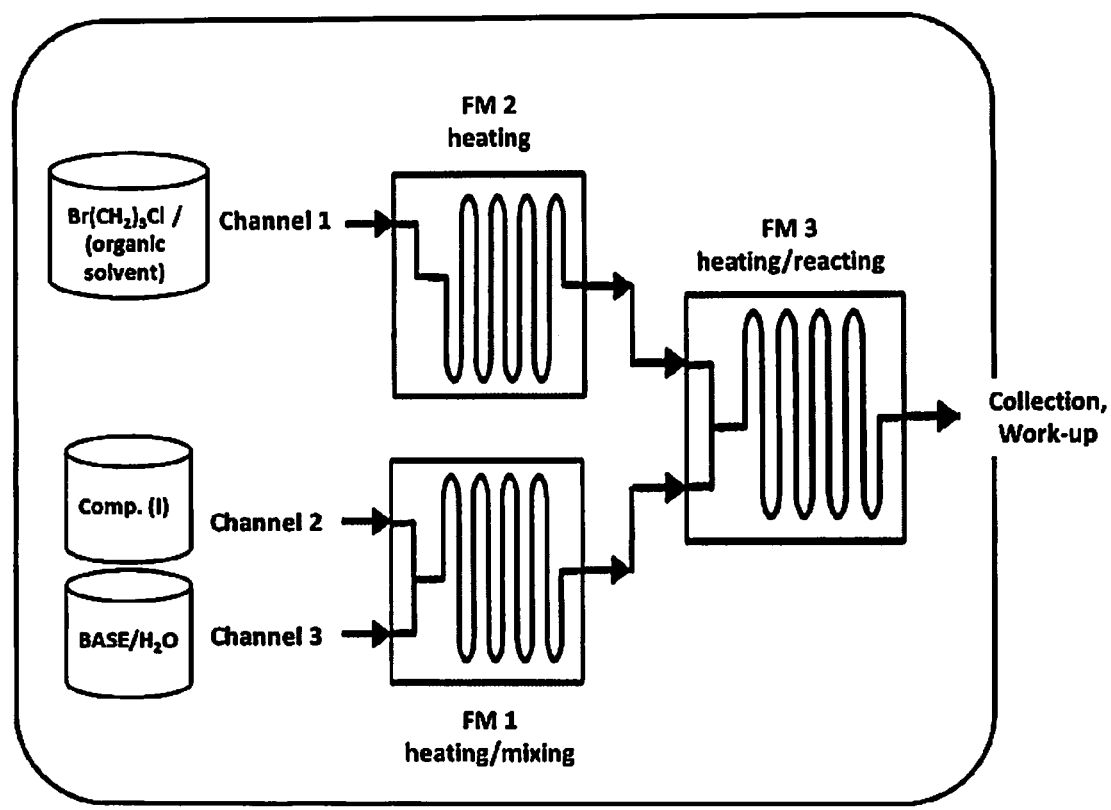
FIG. 1 depicts a schematic representation of a preferred embodiment of the continuous process for the preparation of N-(3-chlorophenyl)-N'-(3-chloropropyl)-piperazine (II) (see step 1, Scheme 1) carried out in a flow-reactor.

As used herein, the term "flow reactor" means a system in which a chemical reaction is run in a continuously flowing stream, and the resulting reaction mixture is continuously collected, in contrast to a batch reactor.

As used herein, the term "continuous process" means a process in which at least one synthetic reaction is performed in a flow reactor in a continuous mode.

As used herein, the terms "continuously" means operations run on a continuous flow (materials or time) basis, in contrast to batch, intermittent, or sequenced operations. In embodiments of the present invention, the terms "continuous", "continuously", and the like, can mean a mode of addition of a solution comprising one or more reactant in such a manner so as to maintain an effective concentration of said one or more reactant in the reaction mixture substantially continuously. Incremental addition of solution which does not substantially affect the nature of the product is still "continuous" as that term is used herein.

As used herein, the term "residence time(s)" means the average length of time a particle of reactant spends within a vessel (as defined at page 458 of McGraw-Hill Dictionary of Engineering, 2E, Copyright (C) 2003 by The McGraw-Hill Companies, Inc.).

As used herein, the terms "fluidic device" or "fluidic module" and the like, mean a device that operates by the interaction of streams of fluid (as defined at page 228 of McGraw-Hill Dictionary of Engineering, 2E, Copyright (C) 2003 by The McGraw-Hill Companies, Inc.).

As used herein, the term "about" is intended to refer to a range when a point value is given, wherein the range comprises at least a 2%+/− of the given value.

As used herein, the term "channel" is intended to refer to any entry point of a reactor, such as a tube, an inlet, etc.

As used herein, the terms "conversion yield(s)", "conversion rate(s)", and "conversion", mean the amount of product formed in the reaction mixture, calculated by HPLC vs standard solution.

DETAILED DESCRIPTION

According to a main aspect, the present invention relates to a continuous process for the preparation of trazodone base (IV) starting from N-(3-chlorophenyl)-N'-(3-chloropropyl)-piperazine (II) and s-triazolo-[4,3-a]-pyridin-3-one (III) according to the reaction scheme below (Scheme 2), comprising continuously mixing in a flow reactor an alkaline aqueous solution of s-triazolo-[4,3-a]-pyridin-3-one (III) and an organic solution of N-(3-chlorophenyl)-N'-(3-chloropropyl)-piperazine (II), and continuously recovering trazodone base (IV), preferably with a conversion yield of at least 70%, more preferably at least 80%, even more preferably 90%. Even more preferably conversion yields are equal or above 95%, 97%, 98%, 99% or quantitative.

Preferably, the ratio of said organic and said alkaline aqueous solution in the reactor is of from about 2:1 to about 1:2.

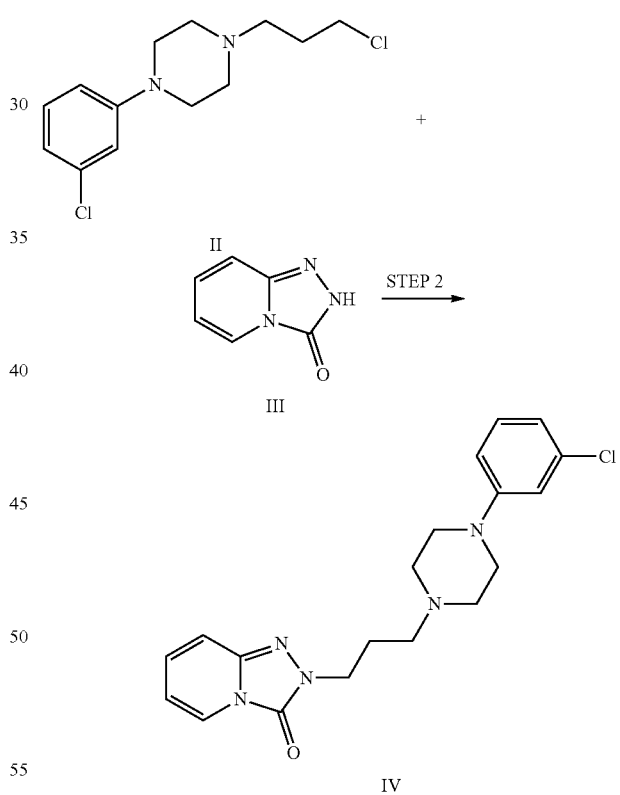

In particular, the invention relates to a continuous process for the preparation of trazodone according to the reaction scheme above (Scheme 2), which comprises:
(i) continuously feeding a first channel of a flow reactor with an aqueous solution of s-triazolo-[4,3-a]-pyridin-3-one (III) and at least one basic compound;
(ii) continuously feeding a second channel of said flow reactor with an organic solution of N-(3-chlorophenyl)-N'-(3-chloropropyl)-piperazine (II) in at least one organic solvent;

(iii) continuously reacting said s-triazolo-[4,3-a]-pyridin-3-one (III) with said N-(3-chlorophenyl)-N'-(3-chloropropyl)-piperazine (II) by continuously mixing said alkaline aqueous solution and said organic solution in said flow reactor, at a temperature of at least 90° C., preferably with a residence time not higher than 180 seconds and of at least 70 seconds; and (iv) continuously collecting said reaction mixture from said flow reactor and isolating the trazodone base (IV).

Preferably the ratio of said organic and said alkaline aqueous solution in step iii) is of from about 2:1 to about 1:2.

The collected reaction mixture can be analysed, e.g. by HPLC, in order to determine the conversion rate and trazodone base (IV) is then isolated from the mixture by standard techniques, e.g. by separating the organic and aqueous phases and concentrating, e.g. by evaporation or distillation, the organic phase to obtain an orange oily residue, which treated, e.g. with isobutanol, yields trazodone base (IV) by precipitation after cooling.

Scheme 3

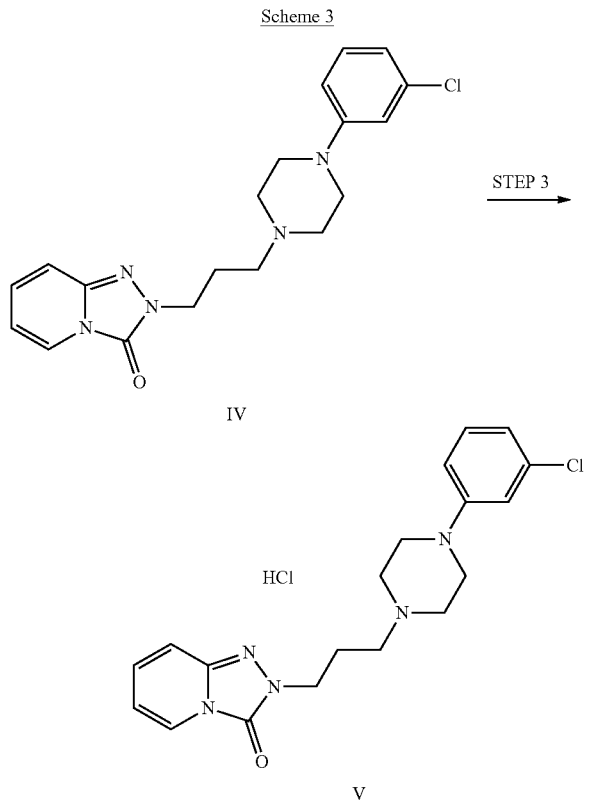

According to a preferred embodiment of the present invention, trazodone base (IV) is then converted into its corresponding salt, trazodone hydrochloride (V) (step 3, Scheme 3), according to step v), which is carried out by dissolving trazodone base (IV) in at least one organic solvent and treating with hydrochloric acid to obtain precipitation of trazodone hydrochloride (V) crystals.

The precipitate of trazodone hydrochloride (V) is then filtered, washed, and dried according to the techniques known by a person skilled in the art.

Thus trazodone base (IV), obtained with the continuous process of the present invention, is characterized by a quality that allows the direct conversion to trazodone hydrochloride (V), without the need for further purification steps required when trazodone base is obtained with common batch processes.

Trazodone HCl (V) is obtained with high purity, and with an extremely low level of alkylating substances, said low level being not higher than 15 ppm, preferably 10 ppm even more preferably 5 ppm, and more preferably below 2.5 ppm, and at least comparable to that disclosed in EP2178850B1, without the need for further purification.

Therefore, according to step i) of the process, s-triazolo-[4,3-a]-pyridin-3-one (III) is dissolved in the alkaline aqueous solution, at a concentration of from 0.3 M to 1.5 M, preferably from 0.5 M to 1.0 M, even more preferably from 0.6 M to 0.8 M.

In a preferred embodiment, said s-triazolo-[4,3-a]-pyridin-3-one (III) is dissolved in said alkaline aqueous solution at a concentration of about 0.6-0.8 M.

Preferably, the solution of said s-triazolo-[4,3-a]-pyridin-3-one (III) is prepared in order to achieve in iii) a molar ratio of from 0.8 to 2.0 mol per mol of N-(3-chlorophenyl)-N'-(3-chloropropyl)-piperazine (II), more preferably from 1.0 to 1.6 mol per mol of N-(3-chlorophenyl)-N'-(3-chloropropyl)-piperazine (II), and even more preferably from 1.2 to 1.4 mol per mol of N-(3-chlorophenyl)-N'-(3-chloropropyl)-piperazine (II).

In a preferred embodiment, said s-triazolo-[4,3-a]-pyridin-3-one (III) is added in a molar ratio of about 1 mol per mol of N-(3-chlorophenyl)-N'-(3-chloropropyl)-piperazine (II).

Advantageously, the aqueous solution of s-triazolo-[4,3-a]-pyridin-3-one (III) comprises at least one basic compound selected from the group comprising at least one inorganic base, at least one organic base, and mixtures thereof.

Preferably, the inorganic base is selected from the group comprising sodium hydroxide, potassium hydroxide, sodium hydride, sodium amide, sodium carbonate, potassium carbonate, sodium bicarbonate, potassium bicarbonate, sodium phosphate, potassium phosphate, ammonium hydroxide, magnesium oxide, and mixtures thereof.

Preferably, the organic base is selected from the group comprising aliphatic and aromatic amines, preferably, trimethylamine, triethylamine, N,N-diisopropylethylamine, triethanolamine, N,N-dimethylethanolamine, N-methylethanolamine, and mixtures thereof.

Preferably, said basic compound is an inorganic base and is selected from the group comprising: sodium hydroxide, potassium hydroxide, sodium carbonate, and mixtures thereof.

In a more preferred embodiment, the basic compounds are sodium hydroxide and potassium hydroxide.

Preferably, the basic compound is added in a molar ratio of from 1.0 to 1.5 mol per mol of s-triazolo-[4,3-a]-pyridin-3-one (III), more preferably from 1.0 to 1.3 mol per mol of s-triazolo-[4,3-a]-pyridin-3-one (III).

In a preferred embodiment, said basic compound is added in a molar ratio of about 1 mol per mol of s-triazolo-[4,3-a]-pyridin-3-one (III).

Preferably, said basic compound is dissolved in said aqueous solution at a concentration of from 0.3 M to 3.0 M, preferably from 0.5 M to 1.5 M, even more preferably from 0.6 M to 1.0 M.

In a preferred embodiment, said basic compound is dissolved in said aqueous solution at a concentration of about 0.6 to 0.8 M.

According to step ii) of the process, N-(3-chlorophenyl)-N'-(3-chloropropyl)-piperazine (II) is dissolved in an at least one organic solvent at a concentration of from 0.3 M to 1.5 M, preferably from 0.5 M to 1.0 M.

In a preferred embodiment, said N-(3-chlorophenyl)-N'-(3-chloropropyl)-piperazine (II) is dissolved in said at least one organic solvent at a concentration of about 0.6-0.8 M.

Advantageously, said organic solvent in step ii) is selected from the group comprising polar aprotic solvents, preferably dimethylformamide, dimethyl sulfoxide, acetone, tetrahydrofuran, acetonitrile, dioxane; apolar solvents, preferably toluene, diethyl ether; polar protic solvents, preferably methanol, ethanol, propanol, isopropanol, butyl alcohol, isobutyl alcohol, benzyl alcohol; and mixtures thereof.

Preferably, said organic solvent is selected from the group comprising isobutyl alcohol, isopropanol, dioxane, acetonitrile, and mixtures thereof.

In a preferred embodiment, said organic solvent is selected from isobutyl alcohol and acetonitrile.

The ratio of said organic and said alkaline aqueous solution in the reactor is variable and may range from about 2:1 to about 1:2.

Advantageously, said alkaline aqueous solution and said organic solution are continuously fed and mixed in said flow reactor with a residence time of at least 70 seconds, preferably of from 70 to 300 seconds, more preferably of from 100 to 150 seconds.

In a preferred embodiment, said alkaline aqueous solution and said organic solution are continuously fed and mixed in said flow reactor with a residence time of from about 110 to 130 seconds.

Advantageously, said alkaline aqueous solution and said organic solution are continuously fed and mixed in said flow reactor at a temperature of at least 90° C., preferably of from 90° C. to 170° C., more preferably of from 130° C. to 160° C., even more preferably 135° C.-155° C.

In a preferred embodiment, said alkaline aqueous solution and said organic solution are continuously fed and mixed in said flow reactor at a temperature of at least 130° C.

In another preferred embodiment, said alkaline aqueous solution and said organic solution are continuously fed and mixed in said flow reactor at a temperature not higher than 160° C.

For example, with a 1:1 ratio between compound (II) and compound (III), when the reaction is carried out at 125° C. a residence time of about 290 seconds is needed to obtain optimal conversion yields, on the other hand when the reaction is carried out at 150° C. optimal conversion yields are obtained with a residence time of about 115 seconds.

By reading the present specification, together with the enclosed working examples, those of ordinary skills in the art will be able to understand how to adapt reaction conditions such as temperature and residence time, etc., in order to further improve the conversion yields.

Advantageously, the continuous process for the preparation of trazodone base (IV) of the present invention leads to a conversion yield, as measured by HPLC, of at least 70%, more preferably at least 80% even more preferably 90%. Even more preferably conversion yields are equal to or above 95%, 97%, 98% or are quantitative.

Advantageously, the continuous process of the present invention leads to trazodone base (IV) with a yield of at least 65%, preferably of at least 75%, even more preferably of at least 85%.

Advantageously, the continuous process of the present invention leads to trazodone base (IV) with a purity measured by HPLC, of at least 90%, preferably at least 95%, more preferably with a purity equal to or above 96%, 97%, 98% and suitable for its direct conversion into the pharmaceutically active ingredient.

According to a preferred embodiment, the continuous process of the present invention leads to trazodone base (IV) with a purity of at least 99% by HPLC.

Trazodone hydrochloride (V) obtained with the process of the present invention is characterized by a low content of alkylating substances as defined above and preferably, below 2.5 ppm, thus complying with the Pharmacopoeia requirements provided in USP 40 NF 35 (Dec. 1, 2017).

Advantageously, step v) of the process of the present invention is highly efficient and leads to trazodone hydrochloride (V) with a yield of at least 70%, preferably of at least 80%, even more preferably of at least 85%.

In a preferred embodiment, step v) of the process of the present invention leads to trazodone hydrochloride (V) with a yield of about 90%.

Advantageously, step v) of the process of the present invention leads to trazodone hydrochloride (V) with a purity of at least 90%, as measured by HPLC, even more preferably of at least 95%. Even more preferably the purity is equal to or above 96%, 97%, 98%, 99%.

According to a preferred embodiment, the continuous process of the present invention leads to trazodone hydrochloride (V) with a purity of at least 99.5% by HPLC.

Scheme 4

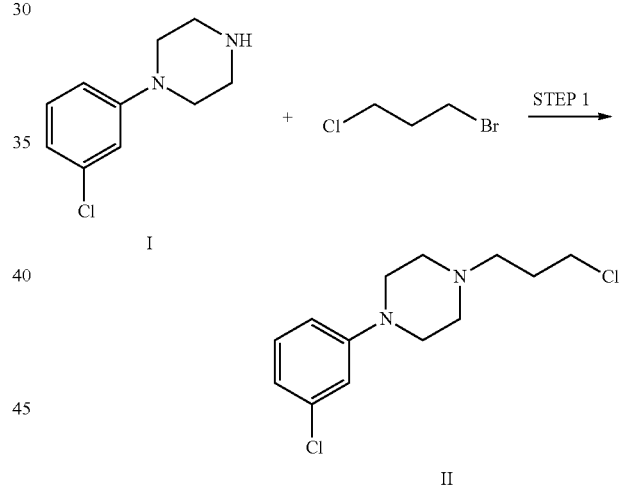

According to a preferred embodiment, the process of the present invention further comprises, and is preceded by, a continuous process for the preparation of N-(3-chlorophenyl)-N'-(3-chloropropyl)-piperazine (II), key intermediate in the synthesis of trazodone, according to reaction scheme above (step 1, Scheme 4), comprising, or consisting, of the following steps:

(a) continuously feeding a first channel of a flow reactor with m-chlorophenyl-piperazine (I) and an aqueous solution of at least one basic compound, to provide an alkaline aqueous phase;

(b) continuously feeding a second channel of said flow reactor with an organic phase of 1-bromo-3-chloropropane optionally in combination with at least one organic solvent;

(c) continuously reacting said m-chlorophenyl-piperazine (I) with said 1-bromo-3-chloropropane by continuously mixing said alkaline aqueous phase and said organic phase in said flow reactor, at a temperature of at least 70° C., preferably with a residence time not higher than 180 seconds and of at least 40 seconds; and (d) continuously removing said reaction mixture from said flow reactor and isolating the obtained product N-(3-chlorophenyl)-N'-(3-chloropropyl)-piperazine base (II).

The product can be isolated with the following procedure: the organic and aqueous phases are separated and water is added to the organic phase. The pH of the mixture is neutralized with an acid. The aqueous phase is discharged and evaporation of the organic solvent under vacuum affords compound (II) as an oily residue.

The obtained N-(3-chlorophenyl)-N'-(3-chloropropyl)-piperazine base (II) is then used as such, without the need to convert it into the hydrochloride form, for the subsequent preparation of trazodone base (IV) (Scheme 1, step 2).

(b) continuously feeding a second channel of said flow reactor with an organic phase of 1-bromo-3-chloropropane optionally in combination with at least one organic solvent;

(c) continuously reacting said m-chlorophenyl-piperazine (I) with said 1-bromo-3-chloropropane by continuously mixing said alkaline aqueous phase and said organic phase in said flow reactor, at a temperature of at least 70° C., preferably with a residence time not higher than 180 seconds and of at least 40 seconds; and (d) continuously removing said reaction mixture from said flow reactor and isolating the obtained product N-(3-chlorophenyl)-N'-(3-chloropropyl)-piperazine (II) which is further admixed with at least one organic solvent;

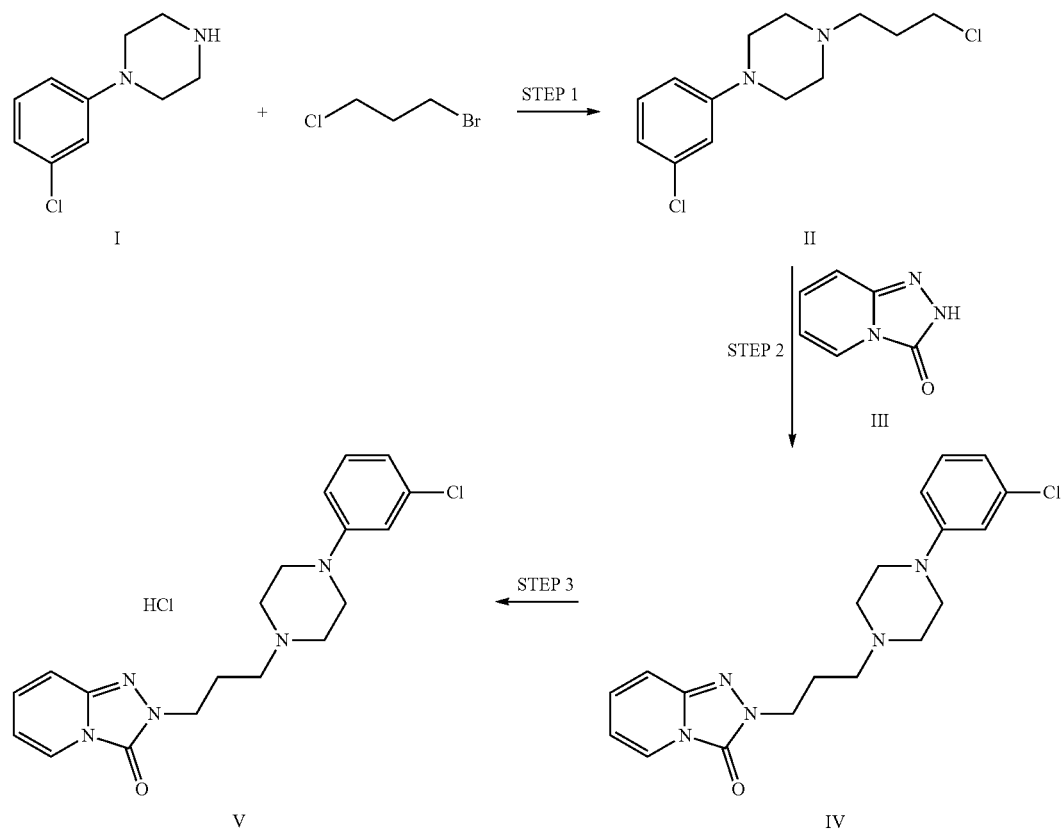

Scheme 1

According to this preferred embodiment the continuous process comprises steps i)-iv) and optionally step v) as defined above, so that the full process for the preparation of trazodone base (IV) and/or trazodone hydrochloride (V), starting from m-chlorophenyl-piperazine (I) and 1-bromo-3-chloropropane, carried out according to Scheme 1 above, comprises the following phases:

(a) continuously feeding a first channel of a flow reactor with m-chlorophenyl-piperazine (I) and an aqueous solution of at least one basic compound, to provide an alkaline aqueous phase;

(i) continuously feeding a first channel of a flow reactor with an aqueous solution of s-triazolo-[4,3-a]-pyridin-3-one (III) and at least one basic compound;

(ii) continuously feeding a second channel of said flow reactor with an organic solution of N-(3-chlorophenyl)-N'-(3-chloropropyl)-piperazine (II) and at least one organic solvent;

(iii) continuously reacting said s-triazolo-[4,3-a]-pyridin-3-one (III) with said N-(3-chlorophenyl)-N'-(3-chloropropyl)-piperazine (II) by continuously mixing said alkaline aqueous solution and said organic solution in said flow reactor, at a temperature of at least 90° C., preferably with a residence time not higher than 180 seconds and of at least 70 seconds; and (iv) continuously removing said reaction mixture from said flow reactor and isolating the obtained product trazodone base (IV), which is preferably converted into its corresponding salt, trazodone hydrochloride (V) (step 3, Scheme 1), according to step v), wherein reagents, reactants and organic solvents are as defined above for steps i)-iv) and v).

Advantageously, according to step a) of the process, the aqueous solution comprises at least one basic compound selected from the group comprising at least one inorganic base, at least one organic base, and mixtures thereof.

Preferably, the inorganic base is selected from the group comprising sodium hydroxide, potassium hydroxide, sodium carbonate, potassium carbonate, sodium bicarbonate, potassium bicarbonate, sodium phosphate, potassium phosphate, ammonium hydroxide, magnesium oxide, hydrazine, hydroxylamine, and mixtures thereof.

Preferably, the organic base is selected from the group comprising, preferably trimethylamine, triethylamine, N,N-diisopropylethylamine, triethanolamine, N,N-dimethylethanolamine, quinoline, pyridine, morpholine, N-methylmorpholine, and mixtures thereof.

Preferably, said basic compound is selected from the group comprising sodium hydroxide, potassium hydroxide, triethylamine, N,N-diisopropylethylamine, and mixtures thereof.

In a preferred embodiment, said basic compound is sodium hydroxide.

Preferably, said basic compound is added in a molar ratio of from 0.8 to 3.0 mol per mol of m-chlorophenyl-piperazine (I), more preferably from 0.9 to 2.0 mol per mol of m-chlorophenyl-piperazine (I), and even more preferably from 1.0 to 1.5 mol per mol of m-chlorophenyl-piperazine (I).

In a preferred embodiment, said basic compound is added in a molar ratio of about 1.1 mol per mol of m-chlorophenyl-piperazine (I).

Preferably, said basic compound is dissolved in said aqueous solution at a concentration of from 1.0 M to 11.0 M, preferably from 1.3 M to 10.5 M, even more preferably from 8.0 M to 10.0 M.

In a preferred embodiment, said basic compound is dissolved in said aqueous solution at a concentration of about 9.5 M.

According to step b) as defined above, advantageously, 1-bromo-3-chloropropane is added in a molar ratio of from 1.0 to 5.0 mol per mol of m-chlorophenyl-piperazine (I), more preferably from 1.5 to 4.0 mol per mol of m-chlorophenyl-piperazine (I), and even more preferably from 2.5 to 3.5 mol per mol of m-chlorophenyl-piperazine (I).

In a preferred embodiment, said 1-bromo-3-chloropropane is added in a molar ratio comprised from about 3.0 to about 4.0 mol per mol of m-chlorophenyl-piperazine (I).

In this regard, the Applicant has defined that the optimal molar ratio of alkylating agent per mol of m-chlorophenyl-piperazine (I) ranges from about 1.5 to 4.0 mol, and even more preferably from 2.5 to 3.5 mol.

Advantageously, the organic solvent optionally combined to 1-bromo-3-chloropropane in the organic phase, as defined in step b) of the process, is used in an amount of from 10% to 20% by weight, with respect to the total weight of said organic phase.

In a preferred embodiment, said organic solvent is used in an amount of from 15% to 20% by weight, with respect to the total weight of said organic phase.

Advantageously, said organic solvent is selected from the group comprising polar aprotic solvents, preferably N-methylpyrrolidone, dimethylformamide, dimethyl sulfoxide, acetone, ethyl acetate, tetrahydrofuran, acetonitrile; and apolar solvents, preferably toluene, benzene, diethyl ether; and mixtures thereof.

In a preferred embodiment, said organic solvent is N-methylpyrrolidone.

Advantageously, said alkaline aqueous phase and said organic phase are continuously fed and mixed in said flow reactor with a residence time of at least 40 seconds, preferably of from 50 to 120 seconds, more preferably of from 55 to 90 seconds.

In a preferred embodiment, said alkaline aqueous phase and said organic phase are continuously fed and mixed in said flow reactor with a residence time of about 60 seconds.

Advantageously, said alkaline aqueous phase and said organic phase are continuously fed and mixed in said flow reactor at a temperature of at least 70° C., preferably of from 80° C. to 100° C., more preferably of from 85° C. to 95° C.

In a preferred embodiment, said alkaline aqueous phase and said organic phase are continuously fed and mixed in said fluidic module of said flow reactor at a temperature of about 88° C.

According to step d) as defined above, advantageously, the N-(3-chlorophenyl)-N'-(3-chloropropyl)-piperazine (II) obtained with the continuous process of the present invention and isolated as described above, can be used as such, without prior conversion to its HCl salt, in the next continuous process for the preparation of trazodone.

This represents a further advantage, because the product of the reaction, N-(3-chlorophenyl)-N'-(3-chloropropyl)-piperazine (II), is itself an alkylating agent and limiting the handling is safer and allows better compliance to the always more restrictive industrial standards for the manipulation of toxic substances.

Advantageously, the continuous process of the present invention leads to N-(3-chlorophenyl)-N'-(3-chloropropyl)-piperazine (II) with a yield of at least 60%, preferably of at least 70%, even more preferably of at least 80%.

In a preferred embodiment, the continuous process of the present invention leads to N-(3-chlorophenyl)-N'-(3-chloropropyl)-piperazine (II) with a yield of about 85%.

Advantageously, the continuous process of the present invention leads to N-(3-chlorophenyl)-N'-(3-chloropropyl)-piperazine (II) with a purity of at least 80% as determined by HPLC method, preferably of at least 85%, even more preferably of at least 90%.

In a preferred embodiment, the continuous process of the present invention leads to N-(3-chlorophenyl)-N'-(3-chloropropyl)-piperazine (II) with a purity of 95% as determined by HPLC method.

Nevertheless, N-(3-chlorophenyl)-N'-(3-chloropropyl)-piperazine (II) can be produced by common "batch" methods, as described for example in U.S. Pat. No. 5,900,485 or it can be commercially obtained.

Therefore, according to a further embodiment, the process according to the present invention comprises a batch process wherein m-chlorophenyl-piperazine (I) and 1-bromo-3-chloropropane are reacted in batch to provide N-(3-chlorophenyl)-N'-(3-chloropropyl)-piperazine (II), which is isolated, preferably converted to its salt of addition with HCl, and then used to feed the continuous reaction according to steps i)-iv), and preferably i)-v).

Advantageously, the present invention can be carried out using any suitable installations for continuous processes.

Figure 3:
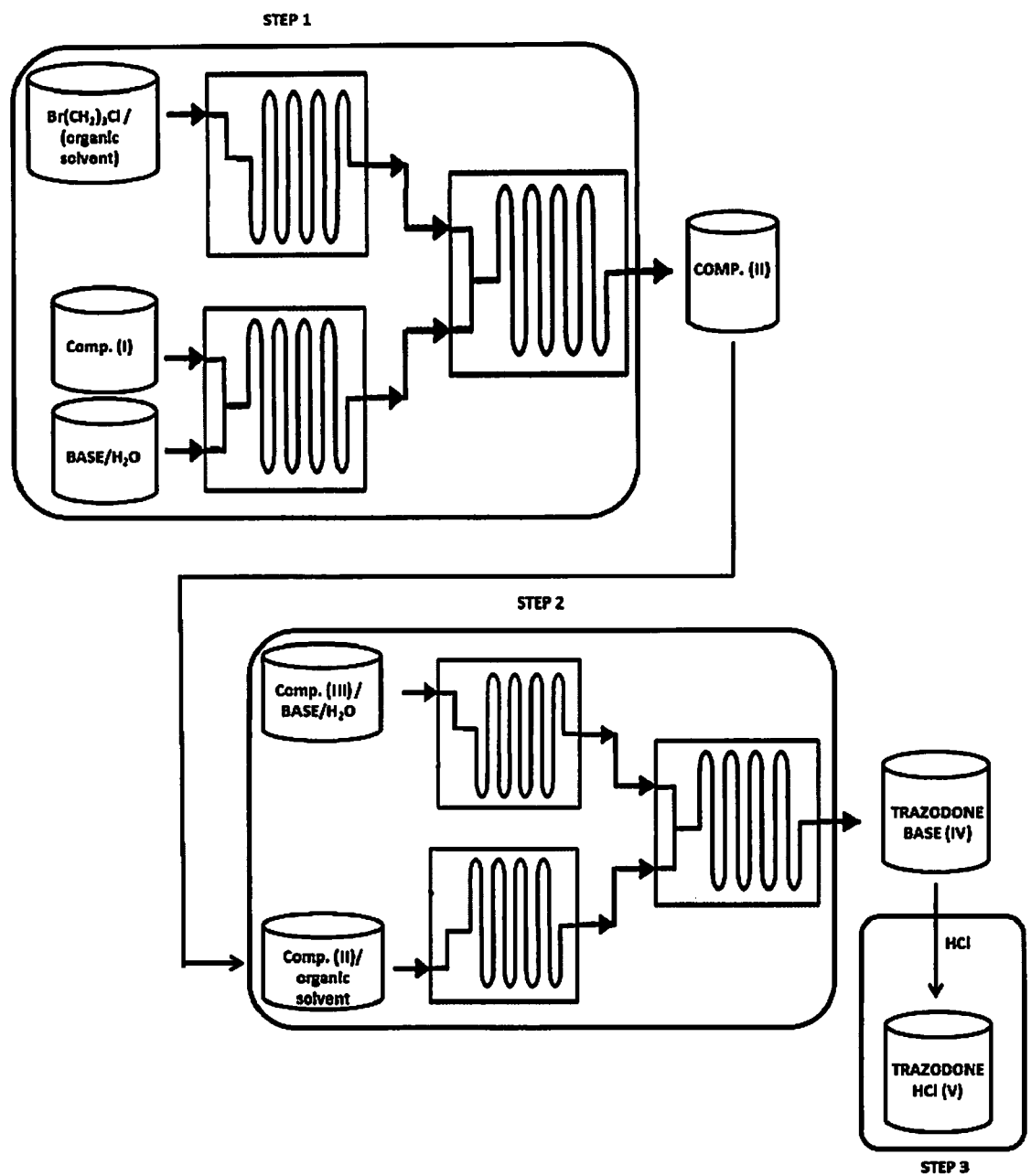
FIG. 3 represents a preferred embodiment of the continuous process for the preparation of Trazodone HCl (V) wherein step 1 and step 2 are carried out in a continuous mode in different flow reactors (Scheme 1), and Step 3 is carried out in a batch mode.
Figure 4:
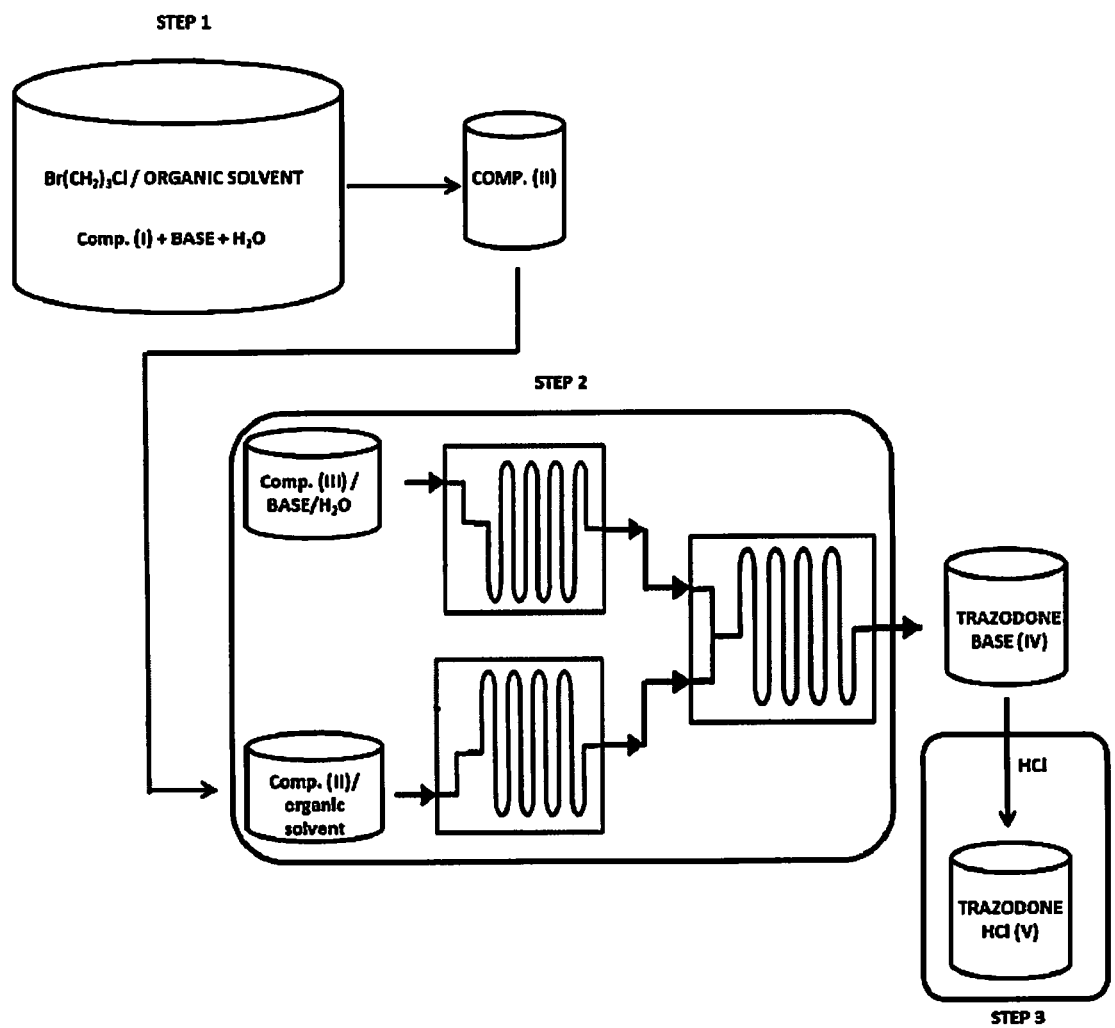
FIG. 4 represents an alternative embodiment of the continuous process for the preparation of Trazodone HCl (V), wherein step 1 and step 3 (Scheme 1) are carried out in a batch mode. Step 2 is carried out in a continuous mode in a flow reactor, according to the main aspect of the present invention.

The flow reactor system where the continuous reactions depicted in scheme 1, steps 1 and 2, are separately carried out and which is described in a specific embodiment disclosed in FIG. 3, is a micro scale flow reactor, preferably microchip flow reactor, microfluidic flow reactor, coil-type flow reactor, tubular flow reactor, plate reactor, packed bed reactor, fluidized bed reactor, fixed bed reactor or is a mesoscale flow reactor or a large scale flow reactor.

Flow reactors systems can be fabricated from an array of materials (glass, silicon, polymers, metals, ceramics) which allow to select the suitable one to perform the organic transformations considering reactants compatibility, conditions and production scale.

Preferably, the flow reactor is a micro-scale, mesoscale or large scale flow reactor selected from the group comprising: microchip flow reactors, microfluidic flow reactors, coil-type flow reactors, tubular flow reactors, plate reactors, packed-bed reactors, fluidized bed reactors and fixed-bed reactors.

Even more preferably, the reactor is selected from the group comprising: microfluidic flow reactors, chip mesoscale flow reactors, coil-type mesoscale flow reactors, large scale flow reactors and their combinations.

According to a preferred embodiment, step 1 is carried out in a ceramic plate continuous flow reactor, and step 2 is carried out in a micro- or mesoscale continuous flow reactor of the chip or chip and coil combined type.

EXAMPLES

General Description of Step 1:

m-chlorophenylpiperazine (I) and 1-bromo-3-chloropropane were continuously reacted in a flow reactor as schematically represented in FIG. 1, to obtain the N-chlorophenyl-N'-propyl-piperazine (II), key intermediate in the synthesis of trazodone.

Compound (I) (channel 2) and an alkaline aqueous solution (channel 3) were used to feed the fluidic module 1 (represented in FIG. 1 as FM1). 1-Bromo-3-chloropropane (3.34 equivalents with respect to compound (I)), or a solution of 1-bromo-3-chloropropane (3.34 equivalents with respect to compound (I)) and N-methylpyrrolidone (NMP) (channel 1) was used to feed the fluidic module 2 (represented in FIG. 1 as FM2).

Both solutions were heated and the compounds were then allowed to react by continuously mixing the two phases in the following modules (represented in FIG. 1 as FM3) at the same temperature.

After collection, compound (II) was isolated from the organic phase by the following work up: the organic and aqueous phases were separated and water was added to the organic phase. The pH of the mixture was neutralized with acid. The aqueous phase was discharged and evaporation of the organic solvent under vacuum afforded compound (II) as an oily residue.

Example 1-3

The procedure reported in the general description of step 1 was used to perform reactions using different alkaline aqueous solutions. The reactor used was a Corning's Advanced-Flow™ Reactor (AFR) G1, equipped with six fluidic modules (9 ml internal volume each), two pre-heating modules and a quenching fluidic module.

Table 1 below shows the reaction conditions used and the results obtained.

TABLE 1

| Sample | T (° C.) | Time (s) | Base (eq.) | Conc. NaOH | Yield (%) | Purity of compound II[a] (%) | Main by-product (%) |
|---|---|---|---|---|---|---|---|
| 1 | 95 | 73 | NaOH (1.1) | 1.7M | 68 | 96.8 | <5 |
| 2 | 95 | 86 | NaOH (1) TEA[b] (0.11) | 1.7M | 70 | 94.6 | <5 |
| 3 | 94 | 73 | TEA[b] (1.1) | — | 65 | 96.3 | <5 |

[a]as measured by HPLC;
[b]TEA: triethylamine

Table 1 shows that all the tested conditions allowed to obtain yields higher than or equal to 65% with a purity above 94%.

Example 4-6

The procedure reported in the general description of step 1 was used to perform reactions at different average temperatures (Table 2). All the reactions were run using a 1.7 M solution of NaOH (1.1 equivalents with respect to m-chlorophenylpiperazine (I)). The reactor used was a Corning's Advanced-Flow™ Reactor (AFR) G1, equipped with six fluidic modules (9 ml internal volume each), two pre-heating modules and a quenching fluidic module.

TABLE 2

| Sample | T (° C.) | Time (s) | Yield (%) | Purity of compound II[a] (%) | Main by-product[a] (%) |
|---|---|---|---|---|---|
| 4 | 77 | 109 | 42 | 98 | <5 |
| 5 | 107 | 112 | 97 | 90 | >5 |
| 6 | 121 | 109 | 100 | 83 | >5 |

[a]measured by HPLC

It appears clearly from the results summarized in the above Table 2 that increasing the temperature led to an increase in yields, but to higher amounts of main by-product and to a decrease in purity.

Examples 7-9

The procedure reported in the general description of step 1 was used to perform reactions where the concentration of the base in the aqueous solution was increased to 9.5 M and the % of NMP varied (Table 3). The reactor used was a Corning's Advanced-Flow™ Reactor (AFR) G1, equipped with six fluidic modules (9 ml internal volume each), two pre-heating modules and a quenching fluidic module.

The reactions were run using a 9.5 M solution of NaOH (1.1 equivalents with respect to m-chlorophenylpiperazine (I)).

TABLE 3

| Sample | T (° C.) | Time (s) | NMP (%) | Yield (%) | Purity of compound II[b] (%) | Main by-product[b] (%) |
|---|---|---|---|---|---|---|
| 7 | 81 | 67 | 10 | 84 | 94.7 | <5 |
| 8 | 88 | 60 | 15 | 84 | 95.2 | <5 |
| 9 | 88 | 60 | 20 | 86 | 95.5 | <5 |

[b]as measured by HPLC

The results summarized in Table 3 show that in all cases it was possible to obtain compound (II) with yields equal to or higher than 84% and a purity of about 95%.

Figure 2:
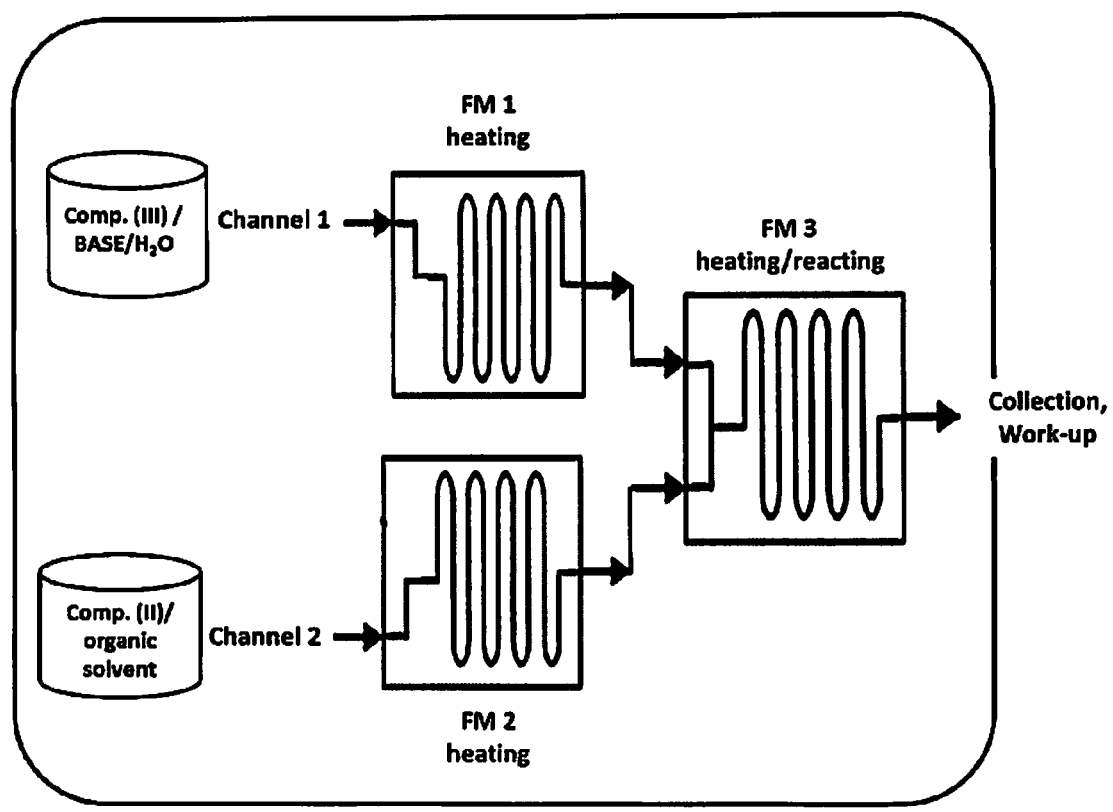
FIG. 2 depicts a schematic representation of a preferred embodiment of the continuous process for the preparation of trazodone base (IV) (see step 2, Scheme 1) carried out in a flow-reactor.

General Description of Step 2:

Compound (II) and s-triazolo-[4,3-a]-pyridin-3-one (III) were continuously reacted in a flow reactor as schematically represented in FIG. 2, to obtain trazodone base (IV).

An alkaline aqueous solution of s-triazolo-[4,3-a]-pyridin-3-one (III) was used to feed channel 1 of a first fluidic module of the flow reactor (depicted as FM1 in FIG. 2). An organic solution of Compound (II) was used to feed channel 2 of a second fluidic module of the flow reactor (depicted as FM2 in FIG. 2).

Both solutions were heated and the compounds were then allowed to react by continuously mixing the two solutions in a third fluidic module of the flow reactor (depicted as FM3 in FIG. 2), at the same temperature.

After collection, to determine the conversion into trazodone base (IV), the mixture was analysed by the HPLC method described in Pharmacopoeia USP 40 NF 35 (Dec. 1, 2017), and the peak related to trazodone base (IV) evaluated against the peaks of a titration curve of a standard solution of pure trazodone base (IV).

Examples 10-15

The procedure reported in the general description of step 2 was used to perform reactions mixing a 0.6 M aqueous solution of compound (III) and NaOH (1 eq.) with a 0.6 M solution of compound (II) in isobutanol, varying the residence time and the average temperature (Table 4). The reactor used was an UltraFlex Labtrix® Start system, Device Type 3227 with PTFE reactor holder, ETFE check valves and FEP tubing.

All the experiments were performed with a compound (III)/compound (II) molar ratio of 1:1.

TABLE 4

| Sample | Time (s) | T (° C.) | Compound IV[a] (%) |
|---|---|---|---|
| 10 | 117 | 125 | 81 |
| 11 | 117 | 150 | 92 |
| 12 | 234 | 125 | 81 |
| 13 | 234 | 150 | 87 |
| 14 | 293 | 125 | 90 |
| 15 | 293 | 150 | 80 |

[a]conversion, as measured by HPLC

Table 4 shows that all the tested conditions allowed to obtain a conversion higher than or equal to 80%.

Example 16-21

The procedure reported in the general description of step 2 was used to perform reactions mixing a 0.6 M aqueous solution of compound (III) and NaOH (1.25 eq.) with a 0.6 M solution of compound (II) in isobutanol, varying the residence time, average temperatures, as well as the flow rate of both solutions in order to obtain different compound (III)/compound (II) molar ratios (Table 5). The reactor used was an UltraFlex Labtrix® Start system, Device Type 3227 with PTFE reactor holder, ETFE check valves and FEP tubing.

TABLE 5

| Sample | Time (s) | T (° C.) | Compound (III)/ Compound (II) ratio | Compound IV[a] (%) |
|---|---|---|---|---|
| 16 | 78 | 125 | 1:1 | 61.6 |
| 17 | 78 | 150 | 1:1 | 86.8 |
| 18 | 117 | 125 | 1.3:1 | 72.6 |
| 19 | 117 | 150 | 1.3:1 | 93.5 |
| 20 | 234 | 125 | 1:1 | 81.6 |
| 21 | 234 | 150 | 1:1 | 77.7 |

[a]conversion, as measured by HPLC

A number of tests were also performed maintaining a molar ratio of 1:1 and varying the flow rate of both solutions in order to obtain an aqueous phase/organic phase ratio of from 2:1 to 1:2. In all cases the results obtained were comparable in terms of conversion rate (by HPLC).

Examples 22-25

The procedure reported in the general description of step 2 was used to perform reactions using acetonitrile as organic solvent.

Table 6 below shows the results obtained performing the reactions mixing a 0.6M alkaline aqueous solution of compound (III) with a 0.6 M solution of compound (II) (compound (III)/compound (II) molar ratio of 1:1) in acetonitrile with a residence time of 117 seconds, varying the average temperature and the base used (Table 6). The reactor used was an UltraFlex Labtrix® Start system, Device Type 3227 with PTFE reactor holder, ETFE check valves and FEP tubing.

TABLE 6

| Sample | T (° C.) | Base (1 eq.) | Compound IV[a] (%) |
|---|---|---|---|
| 22 | 125 | NaOH | 92.2 |
| 23 | 150 | NaOH | >99.0 |
| 24 | 125 | KOH | 71.2 |
| 25 | 150 | KOH | 89.6 |

[a]conversion, as measured by HPLC

Examples 26-29

Also in the case of the reaction performed in acetonitrile, a number of tests were performed maintaining a molar ratio 1:1 and varying the concentration and the flow rate of both solutions in order to obtain an aqueous phase/organic phase ratio of from 2:1 to 1:2. In all cases the results obtained were comparable in terms of conversion rate (as measured via HPLC).

Moreover, reactions were performed mixing an aqueous solution of compound (III) at different concentrations and NaOH or KOH with a 0.6 M solution of compound (II) in acetonitrile with a residence time of 117 seconds, and varying the average temperatures as well as the flow rates in order to obtain different compound (III)/compound (II) molar ratio (Table 7). The reactor used was an UltraFlex Labtrix® Start system, Device Type 3227 with PTFE reactor holder, ETFE check valves and FEP tubing.

TABLE 7

| Sample | T (° C.) | Compound (III)/Compound (II) ratio | Base (eq.)[a] | Conc. (M) Compound III | Compound IV[b] (%) |
|---|---|---|---|---|---|
| 26 | 125 | 1.3:1 | NaOH (1.25) | 0.6 | 96.7 |
| 27 | 150 | 1.3:1 | NaOH (1.25) | 0.6 | 98.3 |
| 28 | 125 | 1:1 | KOH (1.0) | 1.2 | 84.7 |
| 29 | 150 | 1:1 | KOH (1.0) | 1.2 | 94.6 |

[a]with respect to compound III
[b]conversion, as measured by HPLC

Example 30

The procedure reported in the general description of step 2 was used to perform a reaction mixing a 0.6 M aqueous solution of compound (III) and NaOH (1 eq.) with a 0.6 M solution of compound (II), in isobutanol at a temperature of 145° C. and a residence time of 120 seconds, maintaining compound (III)/compound (II) molar ratio 1:1. The reaction was carried out in a Flow Syn UNIQSIS system, equipped with two high pressure pumps delivering reagents into a 2-channel borosilicate glass static mixer chip reactor for reagents pre-heating and pre-mixing, combined with a coil (PTFE—Polytetrafluoroethylene) reactor electrically heated.

The 300 ml volume collected afforded trazodone base (IV) after work-up. Briefly, the phases were separated, and the organic one was concentrated to obtain an orange oily residue, which was diluted in isobutanol.

Trazodone base (IV) was isolated by precipitation after cooling (yellowish solid, yield 66%) and it was analysed by HPLC (purity: 99.4%).

General Description of Step 3:

Trazodone base (IV) prepared as described in step 2 was dissolved in acetone. Water was added and the mixture was heated to about 50° C. under stirring. Then hydrochloric acid (12 N) was added maintaining the temperature below 50° C., up to pH=3-4.

The solution obtained was cooled slowly. When a temperature of 5° C. had been reached, the cooled suspension was filtered on a Buchner filter, washed twice with acetone and the solvent removed under vacuum at 60° C.

The trazodone hydrochloride (V) obtained was analysed by HPLC.

Example 31

The procedure reported in the general description of step 3 was used to prepare the hydrochloride salt of trazodone base (IV) obtained in example 30 (20 g). Trazodone hydrochloride (V) was isolated as an off-white solid, with a yield of 90%, and it was analysed by HPLC (purity 99.8%).

The invention claimed is:

1. A continuous process for the preparation of trazodone base (IV), comprising reacting N-(3-chlorophenyl)-N'-(3-chloropropyl)-piperazine (II) and s-triazolo-[4,3-a]-pyridin-3-one (III), according to reaction scheme 2:

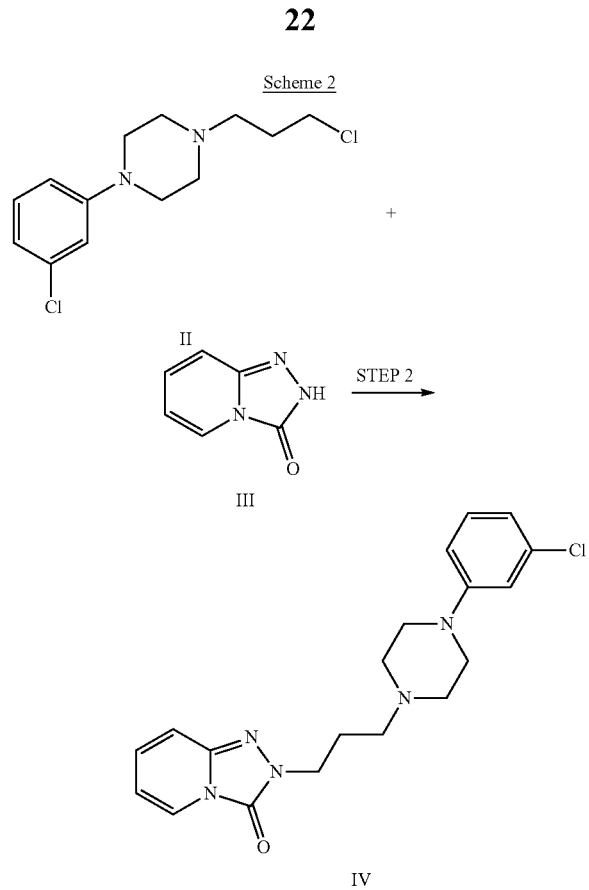

Scheme 2 comprising continuously mixing in a flow reactor an alkaline aqueous solution of s-triazolo-[4,3-a]-pyridin-3-one (III) and an organic solution of N-(3-chlorophenyl)-N'-(3-chloropropyl)-piperazine (II), and continuously recovering trazodone base (IV).

2. The continuous process according to claim 1, comprising:
(i) continuously feeding a first channel of a flow reactor with an aqueous solution of s-triazolo-[4,3-a]-pyridin-3-one (III) and at least one basic compound;
(ii) continuously feeding a second channel of said flow reactor with an organic solution of N-(3-chlorophenyl)-N'-(3-chloropropyl)-piperazine (II) in at least one organic solvent;
(iii) continuously reacting said s-triazolo-[4,3-a]-pyridin-3-one (III) with said N-(3-chlorophenyl)-N'-(3-chloropropyl)-piperazine (II) by continuously mixing said alkaline aqueous solution and said organic solution in said flow reactor, at a temperature of at least 90° C.; and
(iv) continuously collecting said reaction mixture from said flow reactor, and isolating the obtained product trazodone base (IV).

3. The process according to claim 1, wherein trazodone base (IV) is obtained with a conversion yield of at least 70% by HPLC.

4. The process according to claim 1, wherein trazodone base (IV) has a purity of at least 90% by HPLC.

5. The process according to claim 2, wherein the temperature of said continuously reacting iii) is from 130° C. to 160° C.

6. The process according to claim 2, wherein said basic compound in said continuously feeding a first channel i) is an inorganic base selected from the group consisting of sodium hydroxide, potassium hydroxide, sodium hydride, sodium amide, sodium carbonate, potassium carbonate, sodium bicarbonate, potassium bicarbonate, sodium phosphate, potassium phosphate, ammonium hydroxide, magnesium oxide, and mixtures thereof.

7. The process according to claim 6, wherein said inorganic base is selected from the group consisting of sodium hydroxide, potassium hydroxide, sodium carbonate, and mixtures thereof.

8. The process according to claim 2, wherein said basic compound in said continuously feeding a first channel i) is an organic base selected from the group consisting of an aliphatic amine, an aromatic amine, and mixtures thereof.

9. The process according to claim 8, wherein said organic base is selected from the group consisting of trimethylamine, triethylamine, N,N-diisopropylethylamine, triethanolamine, N,N-dimethylethanolamine, N-methylethanolamine, and mixtures thereof.

10. The process according to claim 2, wherein organic solvent in said continuously feeding a second channel ii) is:
(a) a polar aprotic solvent selected from the group consisting of dimethylformamide, dimethyl sulfoxide, acetone, tetrahydrofuran, acetonitrile, dioxane, and mixtures thereof;
(b) an apolar solvent selected from the group consisting of toluene, diethyl ether, and mixtures thereof; or
(c) a polar protic solvent selected from the group consisting of methanol, ethanol, propanol, isopropanol, butyl alcohol, isobutyl alcohol, benzyl alcohol, and mixtures thereof.

11. The process according to claim 2, further comprising:
v) converting said trazodone base (IV) to trazodone hydrochloride (V), according to reaction scheme 3:

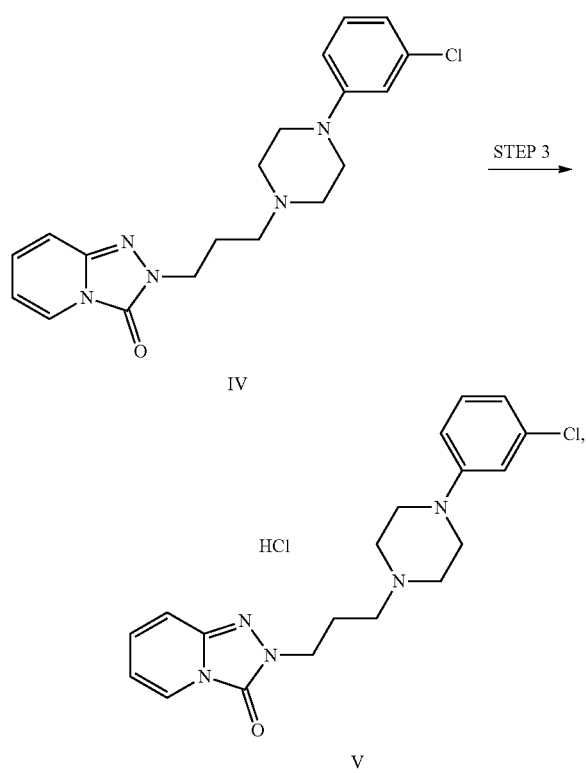

and isolating said trazodone hydrochloride.

12. The continuous process according to claim 1, wherein said N-(3-chlorophenyl)-N'-(3-chloropropyl)-piperazine (II) is prepared by reacting m-chlorophenyl-piperazine (I) with 1-bromo-3-chloropropane, to obtain N-(3-chlorophenyl)-N'-(3-chloropropyl)-piperazine (II) according to reaction scheme 4:

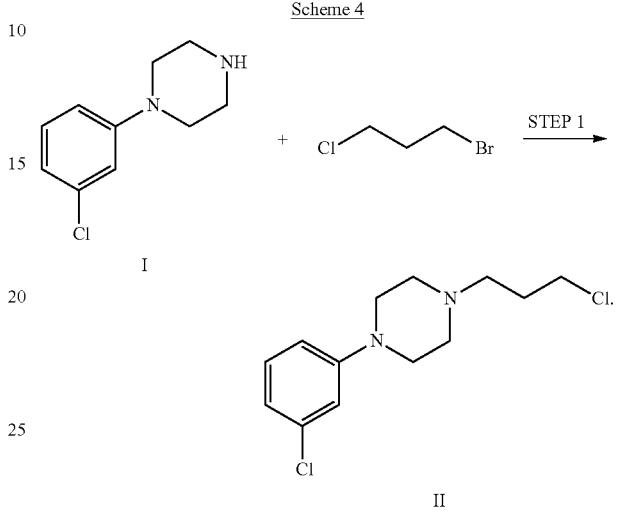

13. The process according to claim 12 wherein m-chlorophenyl-piperazine (I) and 1-bromo-3-chloropropane are reacted in a continuous mode.

14. The process according to claim 12 wherein m-chlorophenyl-piperazine (I) and 1-bromo-3-chloropropane are reacted in a batch mode.

15. The process according to claim 13, comp:
(a) continuously feeding a first channel of a flow reactor with m-chlorophenyl-piperazine (I) and an aqueous solution of at least one basic compound, to provide an alkaline aqueous phase;
(b) continuously feeding a second channel of said flow reactor with an organic phase of 1-bromo-3-chloropropane optionally in combination with at least one organic solvent;
(c) continuously reacting said m-chlorophenyl-piperazine (I) with said 1-bromo-3-chloropropane by continuously mixing said alkaline aqueous phase and said organic phase in said flow reactor, at a temperature of at least 70° C.; and
(d) continuously removing said reaction mixture from said flow reactor and isolating the obtained product N-(3-chlorophenyl)-N'-(3-chloropropyl)-piperazine (II) which is further admixed with at least one organic solvent;
(i) continuously feeding a first channel of a flow reactor with an aqueous solution of s-triazolo-[4,3-a]-pyridin-3-one (III) and at least one basic compound;
(ii) continuously feeding a second channel of said flow reactor with an organic solution of N-(3-chlorophenyl)-N'-(3-chloropropyl)-piperazine (II) and at least one organic solvent;
(iii) continuously reacting said s-triazolo-[4,3-a]-pyridin-3-one (III) with said N-(3-chlorophenyl)-N'-(3-chloropropyl)-piperazine (II) by continuously mixing said alkaline aqueous solution and said organic solution in said flow reactor, at a temperature of at least 90° C.; and (iv) continuously removing said reaction mixture from said flow reactor and isolating the obtained product trazodone base (IV), according to reaction scheme 5:

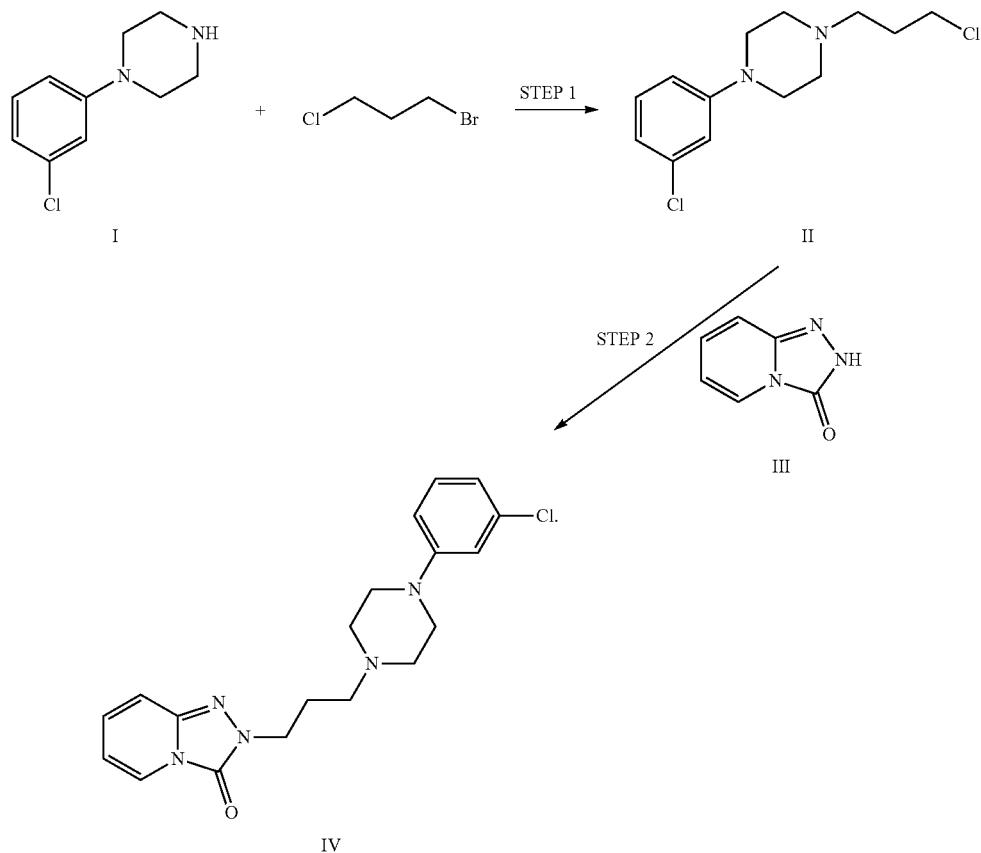

Scheme 5

16. The process according to claim 12, further comprising:
v) converting said trazodone base (IV) to trazodone hydrochloride (V), according to reaction scheme 3:

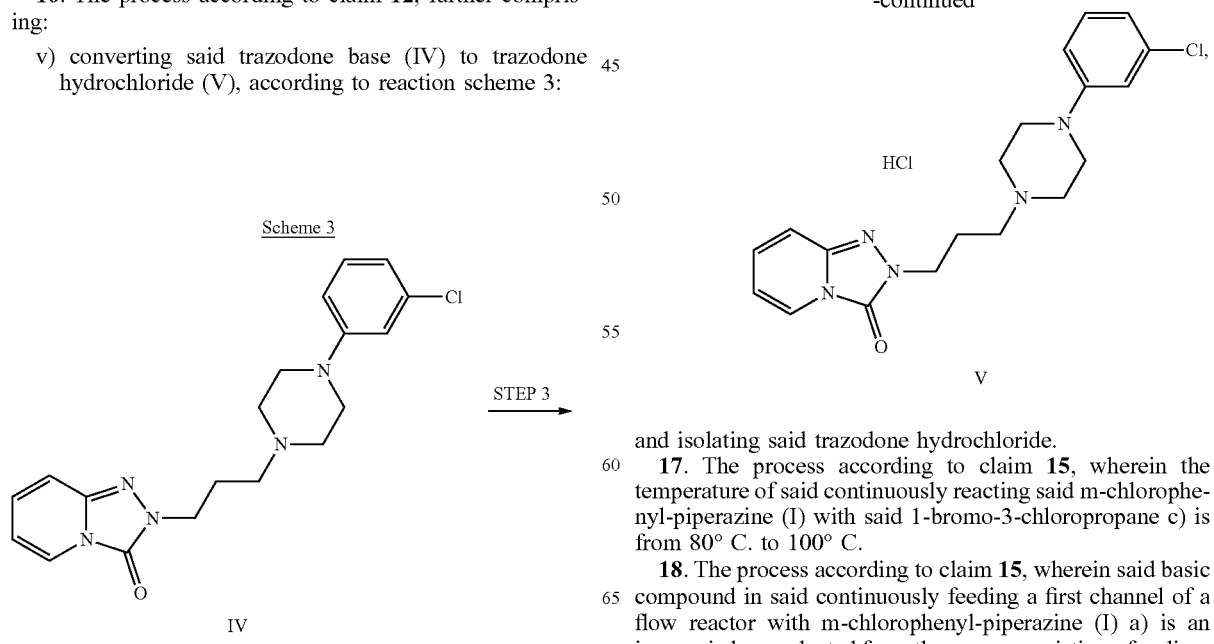

Scheme 3 and isolating said trazodone hydrochloride.

17. The process according to claim 15, wherein the temperature of said continuously reacting said m-chlorophenyl-piperazine (I) with said 1-bromo-3-chloropropane c) is from 80° C. to 100° C.

18. The process according to claim 15, wherein said basic compound in said continuously feeding a first channel of a flow reactor with m-chlorophenyl-piperazine (I) a) is an inorganic base selected from the group consisting of sodium hydroxide, potassium hydroxide, sodium carbonate, potassium carbonate, sodium bicarbonate, potassium bicarbonate, sodium phosphate, potassium phosphate, ammonium hydroxide, magnesium oxide, hydrazine, hydroxylamine, and mixtures thereof.

19. The process according claim 15, wherein said basic compound in said continuously feeding a first channel of a flow reactor with m-chlorophenyl-piperazine (I) a) is an organic base selected from the group consisting of trimethylamine, triethylamine, N,N-diisopropylethylamine, triethanolamine, N,N-dimethylethanolamine, quinoline, pyridine, morpholine, N-methylmorpholine, and mixtures thereof.

20. The process according to claim 15, wherein said organic solvent in said continuously feeding a second channel of said flow reactor with an organic phase of 1-bromo-3-chloropropane b) is:
   (1) a polar aprotic solvent selected form the group consisting of N-methylpyrrolidone, dimethylformamide, dimethyl sulfoxide, acetone, ethyl acetate, tetrahydrofuran, acetonitrile, and mixtures thereof; or
   (2) an apolar solvent selected form the group consisting of toluene, benzene, diethyl ether, and mixtures thereof.

21. The continuous process according to claim 2, wherein:
   said basic compound is sodium hydroxide or triethylamine;
   said organic solvent in said organic solution is isobutyl alcohol, acetonitrile, or toluene.

\* \* \* \* \*